United States Patent [19]
Pettit et al.

[11] Patent Number: 5,635,483
[45] Date of Patent: Jun. 3, 1997

[54] TUMOR INHIBITING TETRAPEPTIDE BEARING MODIFIED PHENETHYL AMIDES

[75] Inventors: George R. Pettit, Paradise Valley, Ariz.; Jozsef Barkoczy, Budapest, Hungary

[73] Assignee: Arizona Board of Regents acting on behalf of Arizona State University, Tempe, Ariz.

[21] Appl. No.: 985,827

[22] Filed: Dec. 3, 1992

[51] Int. Cl.$^6$ .............. A61K 38/00; C07K 5/00; C07K 7/00; C07K 17/00
[52] U.S. Cl. .............................. 514/17; 530/330
[58] Field of Search .................... 514/17; 530/330

[56] References Cited

U.S. PATENT DOCUMENTS 4,816,444  3/1989  Pettit et al. ................ 514/17

OTHER PUBLICATIONS

J. Biol. Chem. vol. 266, No. 24 (Aug. 25, 1991) pp. 15882–15889.
Biochem. Pharm. vol. 40 No. 8 (Oct. 15, 1990) pp. 1859–1864.
*The Peptides* vol. 2 Gross & Meinnhofer (Acad. Press 1980) pp. 102–103.
Tetra. Lett. vol. 32 No. 21 pp. 2395–2398 (May 20, 1991).

*Primary Examiner*—Toni R. Scheiner
*Assistant Examiner*—Sheela J. Huff
*Attorney, Agent, or Firm*—Richard R. Mybeck

[57] ABSTRACT

New tetrapeptides bearing modified phenethyl amides are elucidated and synthesized and found to exhibit tumor inhibiting effects when measured against the NCI screen for six major types of human cancer and against the murine P388 lymphocytic cell line. The new modified tetrapeptides phenethyl amides are 6(a–k).

8 Claims, No Drawings

TUMOR INHIBITING TETRAPEPTIDE BEARING MODIFIED PHENETHYL AMIDES

Financial assistance for this project was provided under U.S. Government Grant Number OIG-CA44344-01A1-2. The United States government may own certain rights to this invention.

INTRODUCTION

This invention relates generally to the field of antineoplastic compounds, and more particularly to the design and synthesis of selected tetrapeptides bearing modified phenethylamides, exhibiting tumor inhibitory effects.

BACKGROUND OF THE INVENTION

Ancient marine invertebrate species of the Phyla Bryozoa, Molluska, and Porifera have been well established in the oceans for over one billion years. Such organisms have undergone trillions of biosynthetic reactions of their evolutionary chemistry to reach their present level of cellular organization, regulation and defense.

For example, marine sponges have changed minimally in physical appearance for nearly 500 million years. This suggests a very effective chemical resistance to evolution in response to changing environmental conditions over that period of time. Recognition of the potential for utilizing this biologically potent marine animal for medicinal purposes was recorded in Egypt about 2,700 BC and by 200 BC sea hare extracts were being used in Greece for their curative affect. This consideration along with the observation that marine animals, e.g. invertebrates and sharks, rarely develop cancer led to the systematic investigation of marine animal and plant anticancer compounds.

By 1968 ample evidence had been obtained, based on the U.S. National Cancer Institute's (NCI) key experimental cancer study systems, that certain marine organisms could provide new and antineoplastic and/or cytotoxic agents and might also lead to compounds which would be effective in the control and/or eradication of viral diseases.

Further, these marine organisms were believed to possess potentially useful drug candidates of unprecedented structure which had eluded discovery by other methods of medicinal chemistry. Fortunately, these expectations have been realized, e.g. the discovery of the bryostatins, dolastatins and cephalostatins, many of which are now in preclinical development or human clinical studies.

Those researchers presently involved in medicinal chemistry know well the time lag between the isolation of a new compound and its introduction to the market. Often this procedure takes several years and may take decades. As a result, industry, in association with the U.S. Government, has developed a system of testing criteria which serves two purposes. One is to eliminate those substances which are shown through testing to be economically counterproductive. The second, more important purpose serves to identify those compounds which demonstrate a high likelihood of success and therefore warrant the further study and qualification, and attendant expense, necessary to meet the stringent regulatory requirements which control the ultimate market place.

The current cost to develop the necessary data approaches ten million dollars per compound. As such, economics dictate that such a huge investment will be made only when there is a reasonable opportunity for it to be recovered. Absent such opportunity, there will be no investment and the research involving the discovery of these potentially life saving compounds will cease. Only two hundred years ago many diseases ravaged mankind. Many of these now have been controlled or eradicated. During the advancement of means to treat or eliminate these diseases, work with appropriate animals was of critical importance.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and has been accepted in scientific circles. The protocol, and the established statistical means for analyzing the results obtained by the standardized testing are fully described in the literature. See: Body, Dr. Michael R., *Principles & Practice of Oncology*, PPO Updates, Volume 3, Number 10, October 1989, for an in depth description of the testing protocol; and Paull, K. D., "Display and Analysis of Patterns of Differential Activity of Drugs Against Human Tumor Cell Lines; Development of Mean Graph and COMPARE Algorithm", *Journal of the National Cancer Institute Reports*, Vol. 81, No. 14, Page 1088, Jul. 14, 1989 for a description of the methods of statistical analysis. Both of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures possessing antineoplastic qualities. The collection and processing of these later compounds from their natural sources ranges from grossly impractical to the utterly impossible. Ignoring the ecological impact, the population of these creatures and the cost of collection and extraction make the process unworkable. Artificial synthesis of the active compounds is the only possible solution.

Therefore, the elucidation of the structure of these antineoplastic compounds is essential. After the structure has been determined, then a means of synthesis must be determined. This is often a long and arduous procedure due to the idiosyncratic complexity of these naturally occurring, evolutionary modified compounds. In addition, research is necessary to determine whether any portion of the naturally occurring compound is irrelevant to the desired properties, so that focus can be on the simplest structure having the perceived properties.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The impairment of human cancerous tumor growth is utilitarian in that it relieves these conditions, thereby allowing the human thus affected to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive for further research.

The recognition of antineoplastic and tumor inhibiting activity as demonstrated by accepted NCI criteria as "utility" can promote research efforts in the United States and is unequivocally essential if those efforts are to obtain even a modest modicum of success.

BRIEF DESCRIPTION OF THE INVENTION

Various species of sponges and sea hares produce cyclic and linear peptides that contain amino acids which have been shown to be effective in the treatment and/or control of cancer in humans. For example, Dolastatin 10 (U.S. Pat. No. 4,816,444), which has only recently been synthesized, has proven to be a potent antineoplastic substance. This finding, in turn, has prompted research into other compounds related to Dolastatin 10.

Accordingly a principle object of this invention is to provide a new agent useful in the retardation or remission of one or more types of cancer.

A further object of the present invention is to provide methods and procedures for designing and synthesizing selected tetrapeptides bearing modified phenethylamides for the treatment of neoplastic diseases and the inhibition of tumor growth.

These and still further objects, as shall hereinafter appear, are readily fulfilled by the present invention in a remarkably unexpected manner as will be readily discerned from the following detailed description of an exemplary embodiment thereof.

DETAILED DESCRIPTION OF THE INVENTION

The discovery of new types of potentially antineoplastic peptides presents one of the most essential and promising approaches to a synthesis of new anticancer and immunosuppressant drugs. The dolastatins, an unprecedented series of linear and cyclic antineoplastic and/or cytostatic peptides isolated from Indian Ocean sea hare *Dolabella auricularia* (See: Pettit et al., *J. Am. Chem. Soc.*, 1976, 98, 4677) have shown excellent antineoplastic activity. The very productive sea hare *D. auricularia* has produced many structurally distinct peptides. Presently Dolastatin 10, a linear pentapeptide, represents the most important member as a potentially useful antineoplastic activity profiles against various cancer screens presently known (See: Pettit et al., *J. Am. Chem. Soc.*, 1987, 109, 6883). Recently reported is the total synthesis and absolute configuration of this structurally unique and biologically active peptide (See: Pettit et al., *J. Am. Chem Soc.*, 1989, 111, 5463). Subsequent to this report, this compound attracted considerable interest in the research community (See e.g., Hamada et al., *Tetrahedron Lett.*, 1991, 32, 931. Hayashi et al., *Peptide Chemistry*, 1989, 291 and Tomioka et al., *Tetrahedron Lett.*, 1991, 32(21), 2395–2398).

A series of Dolastatin 10 chiral isomers has been documented (See: Pettit et al., *J. Med. Chem.*, 1990, 33, 3132). More recently these experiments were extended to synthesis of R-Doe-isodolastatin 10. We have now found that the R-dolaphenine (Doe) substitution does not result in any significant difference in its human cancer cell line activity when compared with Dolastatin 10. This fact suggested that the 2-thiazolyl unit could be replaced with a simple amide. The amide molecular length was then examined, starting with benzylamine, phenethylamine and 3-phenyl-1-propylamine. Also studied was a systematic series of modifications at the dolaphenine position introducing a substituted nitrogen instead of a phenyl ring.

Then, fixing the length of the side chain at n=2 shows the importance of substituting the phenyl ring and the aliphatic side chain in the amide part. Next investigated was the role of placing substituents on the phenyl ring using electron withdrawing (4-nitro, 4-chloro, 4-fluoro, 4-bromo, 3-chloro, 2-chloro) and electron releasing (3,4-dimethoxy) groups. The corresponding amine (2a–g) was allowed to react with dolaproine (1). Synthesis of amides 3a–g using diethyl phosphorocyanidate (DEPC) for condensation led to an excellent yield. No racemization was observed during this reaction. Synthesis followed and the (3a–g) amides are shown below:

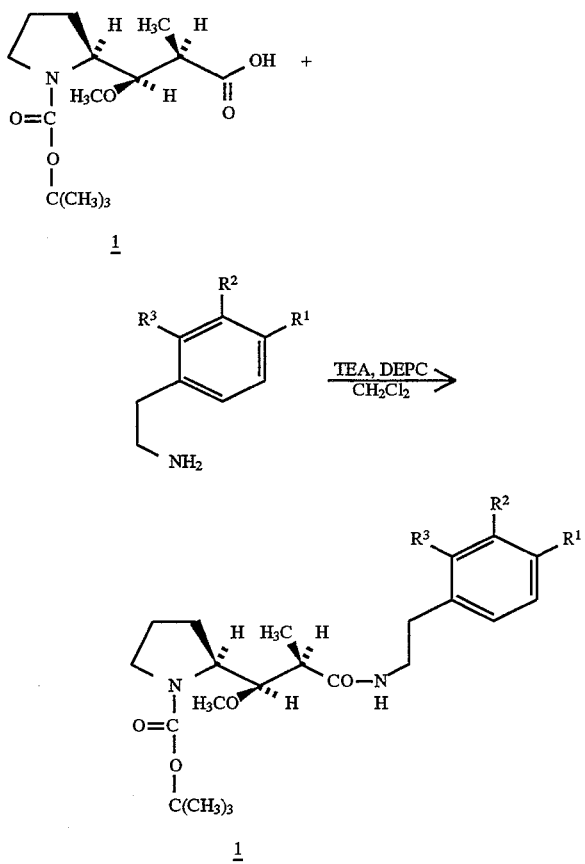

2a ($R^1 = R^2 = OCH_3$, $R^3 = H$)
2b ($R^1 = NO_2$, $R^2 = H$, $R^3 = H$)
2c ($R^1 = Cl$, $R^2 = H$, $R^3 = H$)
2d ($R^1 = F$, $R^2 = H$, $R^3 = H$)
2e ($R^1 = Br$, $R^2 = H$, $R^3 = H$)
2f ($R^1 = H$, $R^2 = Cl$, $R^3 = H$)
2g ($R^1 = H$, $R^2 = H$, $R^3 = Cl$)

3a ($R^1 = R^2 = OCH_3$, $R^3 = H$)
3b ($R^1 = NO_2$, $R^2 = H$, $R^3 = H$)
3c ($R^1 = Cl$, $R^2 = H$, $R^3 = H$)
3d ($R^1 = F$, $R^2 = H$, $R^3 = H$)
3e ($R^1 = Br$, $R^2 = H$, $R^3 = H$)
3f ($R^1 = H$, $R^2 = Cl$, $R^3 = H$)
3g ($R^1 = H$, $R^2 = H$, $R^3 = Cl$)

The protecting groups of amides 3a–g were removed with trifluoroacetic acid to afford the trifluoroacetate salt 4a–g as shown below:

Trifluoroacetate salt 4a–q

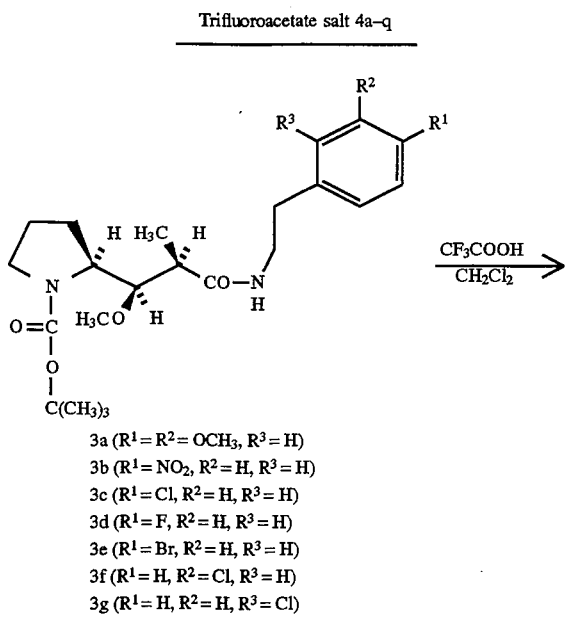

3a (R¹ = R² = OCH₃, R³ = H)
3b (R¹ = NO₂, R² = H, R³ = H)
3c (R¹ = Cl, R² = H, R³ = H)
3d (R¹ = F, R² = H, R³ = H)
3e (R¹ = Br, R² = H, R³ = H)
3f (R¹ = H, R² = Cl, R³ = H)
3g (R¹ = H, R² = H, R³ = Cl)

-continued
Trifluoroacetate salt 4a–q

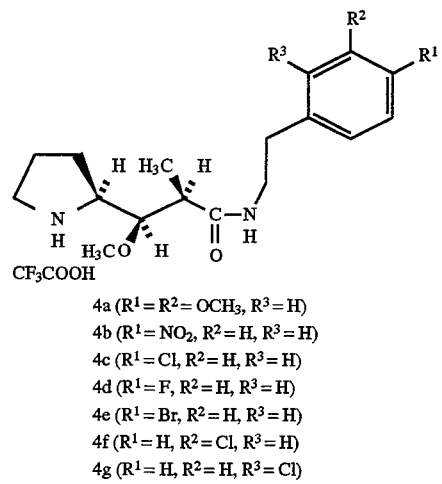

4a (R¹ = R² = OCH₃, R³ = H)
4b (R¹ = NO₂, R² = H, R³ = H)
4c (R¹ = Cl, R² = H, R³ = H)
4d (R¹ = F, R² = H, R³ = H)
4e (R¹ = Br, R² = H, R³ = H)
4f (R¹ = H, R² = Cl, R³ = H)
4g (R¹ = H, R² = H, R³ = Cl)

Diethyl phosphorocyanidate (DEPC) was used again with excellent results for coupling the tripeptide 5 with each of the trifluoroacetate salts 4a–g to yield dolastatin 10 structural modification 6a–g accord to the following reaction:

Synthesis of Peptides 6a–g

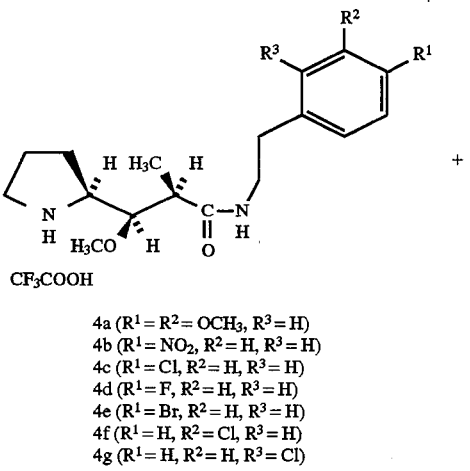

4a (R¹ = R² = OCH₃, R³ = H)
4b (R¹ = NO₂, R² = H, R³ = H)
4c (R¹ = Cl, R² = H, R³ = H)
4d (R¹ = F, R² = H, R³ = H)
4e (R¹ = Br, R² = H, R³ = H)
4f (R¹ = H, R² = Cl, R³ = H)
4g (R¹ = H, R² = H, R³ = Cl)

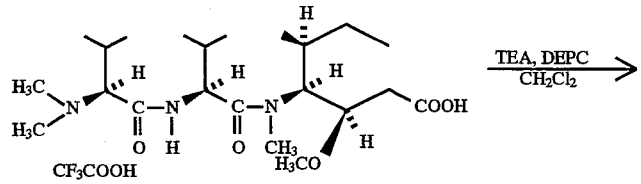

-continued
Synthesis of Peptides 6a–g

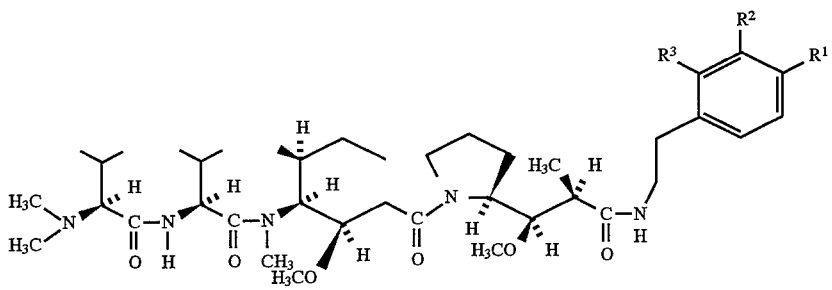

6a (R¹ = R² = OCH₃, R³ = H)
6b (R¹ = NO₂, R² = H, R³ = H)
6c (R¹ = Cl, R² = H, R³ = H)
6d (R¹ = F, R² = H, R³ = H)
6e (R¹ = Br, R² = H, R³ = H)
6f (R¹ = H, R² = Cl, R³ = H)
6g (R¹ = H, R² = H, R³ = Cl)

Next investigated was the effect of substituting the aliphatic chain and the amide nitrogen in the modified dolaphenine position using unsubstituted phenyl ring. Then methyl and hydroxyl substituents were applied starting with (1R, 2R)-2-methylamino-1-phenylpropanol (2h), (1S, 2R)-norephedrine (2i), D(+)-(1S, 2S)-norephedrine (2j), and (1R, 2S)-norephedrine (2k). Synthesis of modified tetrapeptide phenethylamides 6h–k was achieved by the methods developed for amides 6a–g according to the reactions shown below:

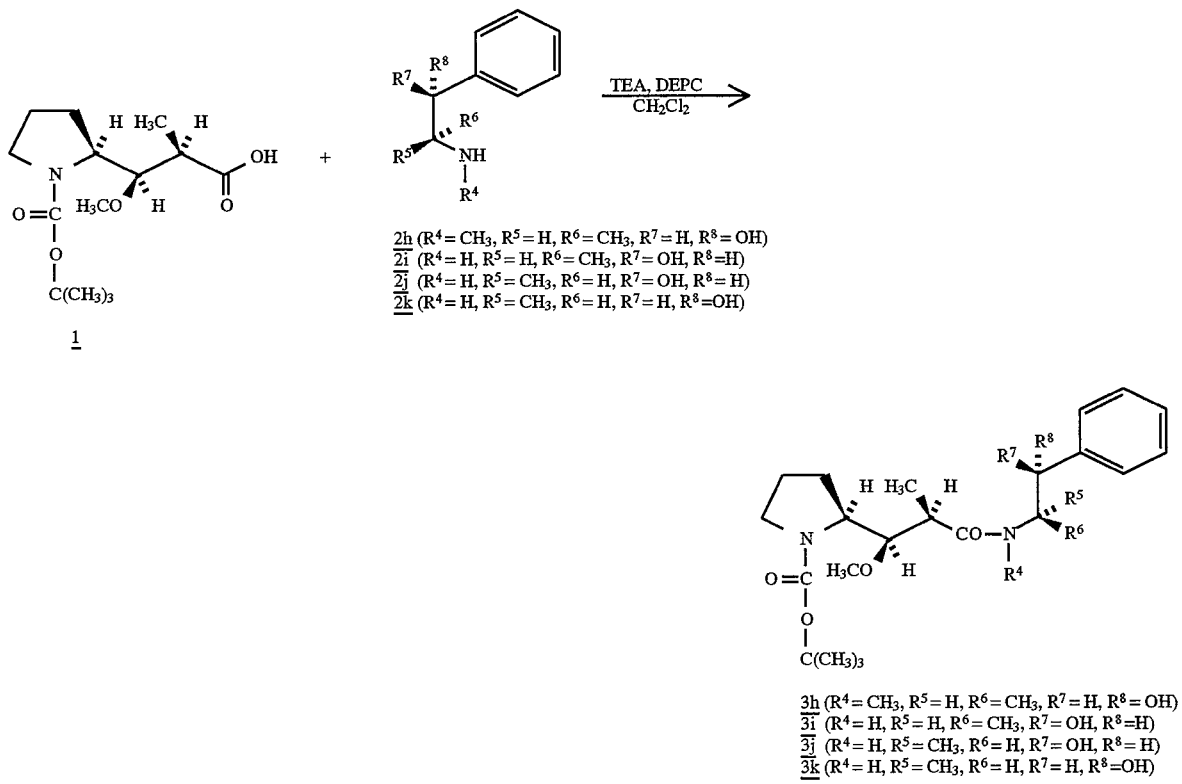

-continued

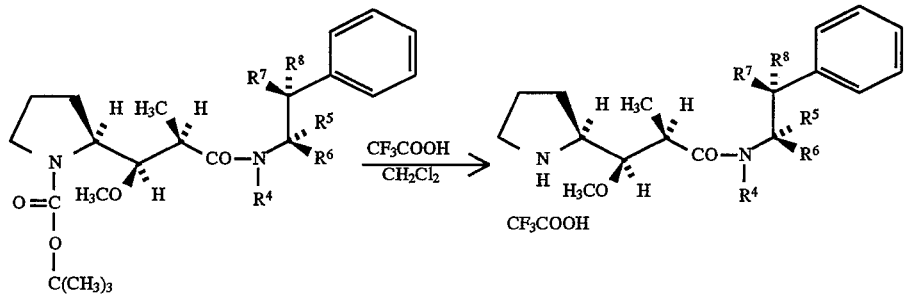

3h (R⁴ = CH₃, R⁵ = H, R⁶ = CH₃, R⁷ = H, R⁸ = OH)
3i (R⁴ = H, R⁵ = H, R⁶ = CH₃, R⁷ = OH, R⁸ = H)
3j (R⁴ = H, R⁵ = CH₃, R⁶ = H, R⁷ = OH, R⁸ = H)
3k (R⁴ = H, R⁵ = CH₃, R⁶ = H, R⁷ = H, R⁸ = OH)

4h (R⁴ = CH₃, R⁵ = H, R⁶ = CH₃, R⁷ = H, R⁸ = OH)
4i (R⁴ = H, R⁵ = H, R⁶ = CH₃, R⁷ = OH, R⁸ = H)
4j (R⁴ = H, R⁵ = CH₃, R⁶ = H, R⁷ = OH, R⁸ = H)
4k (R⁴ = H, R⁵ = CH₃, R⁶ = H, R⁷ = H, R⁸ = OH)

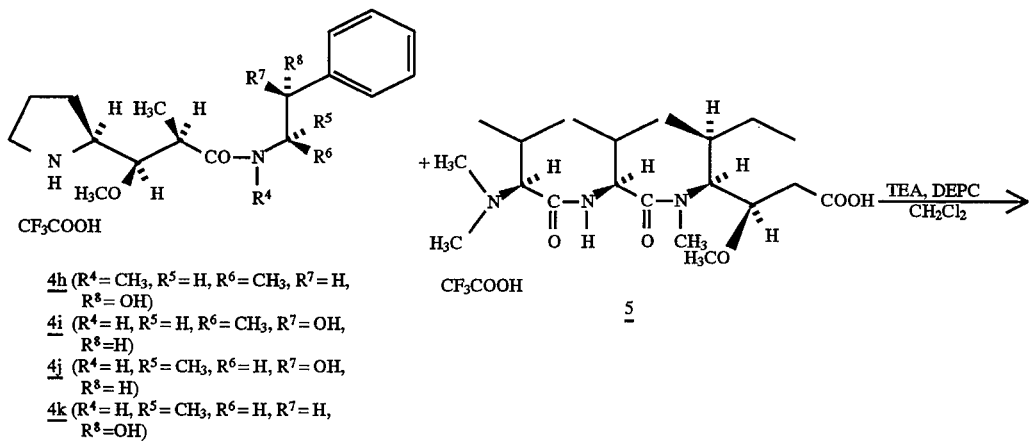

4h (R⁴ = CH₃, R⁵ = H, R⁶ = CH₃, R⁷ = H, R⁸ = OH)
4i (R⁴ = H, R⁵ = H, R⁶ = CH₃, R⁷ = OH, R⁸ = H)
4j (R⁴ = H, R⁵ = CH₃, R⁶ = H, R⁷ = OH, R⁸ = H)
4k (R⁴ = H, R⁵ = CH₃, R⁶ = H, R⁷ = H, R⁸ = OH)

5

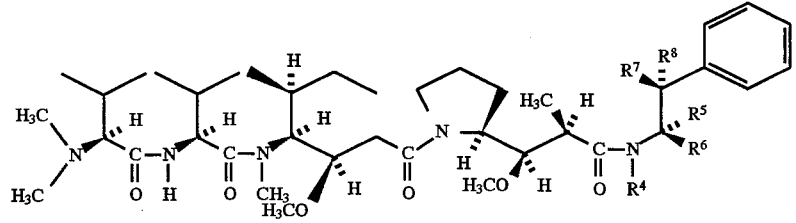

6h (R⁴ = CH₃, R⁵ = H, R⁶ = CH₃, R⁷ = H, R⁸ = OH)
6i (R⁴ = H, R⁵ = H, R⁶ = CH₃, R⁷ = OH, R⁸ = H)
6j (R⁴ = H, R⁵ = CH₃, R⁶ = H, R⁷ = OH, R⁸ = H)
6k (R⁴ = H, R⁵ = CH₃, R⁶ = H, R⁷ = H, R⁸ = OH)

In a preferred embodiment of the present invention, the synthesis of the constituent intermediate structures is performed by the following steps.

Synthesis of Amides 3a–k (shown above). General Procedure A

To a solution of [2S-[2R*(αS*,βS*)]]-1-[(1,1-dimethylethoxy) carbonyl]-B-methoxy-α-methyl-2-pyrrolidinepropanoic acid (t-Boc-Dolaproine, 1, 0.144 g, 0.5 mmol) in dichloromethane (3 ml, distilled from CaH₂) was added the respective amine (2a–k 0.5 mmol) followed by triethylamine (0.077 ml, 0.55 mmol) and diethyl phosphorocyanidate (DEPC, 0.09 ml, 93%, 0.55 mmol, ice bath) and the solution was stirred under argon for two hours. The solvent was removed (under vacuum at room temperature) and the residue was chromatographed (silica gel column using hexane-acetone 3:1 as eluent). After the evaporation of solvent from the fractions (selected by TLC) 2 ml dry dichloromethane was added and evaporation was repeated. The residue was dried in a desiccator under vacuum overnight to afford the amide (3a–k) as a viscous oil.

[2S-[2R*[1S*,2S*]]]-2-[1-methoxy-2-methyl-3-oxo-3-[[2-(3,4-dimethoxy-phenyl)-ethyl]amino]propyl]-1-pyrrolidinecarboxylic acid, 1,1-dimethylethylester (3a)

Compound 3a was synthesized from t-Boc-Dolaproine (1) and 3,4-dimethoxyphenetylamine (2a) according to General Procedure A.

Yield 3a: 0.189 g (84%) [α]_D25=–33 (c=1.6, CHCl₃) Anal. Calcd for C₂₄H₃₈N₂O₆, M.w.: 450.566

[2S-[2R*[1S*, 2S*]]]-2-[1-methoxy-2-methyl-3-oxo-3-[[2-(4-nitro-phenyl)-ethyl]amino]propyl]-1-pyrrolidinecarboxylic acid, 1,1-dimethylethylester (3b)

Compound 3b was synthesized from t-Boc-Dolaproine (1) and 4-nitrophenethylamine (2b) according to General Procedure A.

Yield 3b: 0.176 g (81%) [α]_D25 =–54 (c=0.29 in CHCl₃)
Anal. Calcd for C₂₂H₃₃N₃O₆) M.w.: 435.505

[2S-[2R*[1S*, 2S*]]]-2-[1-methoxy-2-methyl-3-oxo-3-[[2-(4-chloro-phenyl)-ethyl]amino]propyl]-1-pyrrolidinecarboxylic acid, 1,1-dimethylethylester (3c)

Compound 3c was synthesized from t-Boc-Dolaproine (1) and 2-(4-chloro-phenyl)-ethylamine (2c) according to General Procedure A.

Yield 3c: 0.183 g (85.5%) $[\alpha]_D 25=-38$ (c=1.52 in CHCl$_3$) Anal. Calcd for C$_{22}$H$_{33}$N$_2$O$_4$Cl M.w.: 424.953

[2S-[2R*[1S*, 2S*]]]-2-[1-methoxy-2-methyl-3-oxo-3-[[2-(4-fluoro-phenyl)-ethyl]amino]propyl]-1-pyrrolidinecarboxylic acid, 1,1-dimethylethylester (3d)

Compound 3d was synthesized from t-Boc-Dolaproine (1) and 2-(4-fluoro-phenyl)-ethylamine (2d) according to General Procedure A.

Yield 3d: 0.192 g (94.3%) $[\alpha]_D 25=-37.70$ (c=1.61 in CHCl$_3$) M.w.: 408.5 C$_{22}$H$_{33}$N$_2$O$_4$F

[2S-[2R*[1S*, 2S*]]]-2-[1-methoxy-2-methyl-3-oxo-3-[[2-(4-bromo-phenyl)-ethyl]amino]propyl]-1-pyrrolidinecarboxylic acid, 1,1-dimethylethylester (3e)

Compound 3e was synthesized from t-Boc-Dolaproine (1) and 2-(4-bromo-phenyl)-ethylamine (2e) according to General Procedure A.

Yield 3e: 0.193 g (82.1%) $[\alpha]_D 25=-29.67$ (c=1.52 in CHCl$_3$) M.w.: 469.49 C$_{22}$H$_{33}$N$_2$O$_4$Br

[2S-[2R*[1S*, 2S*]]]-2-[1-methoxy-2-methyl-3-oxo-3-[[2-(3-chloro-phenyl)-ethyl]amino]propyl]-1-pyrrolidinecarboxylic acid, 1,1-dimethylethylester (3f)

Compound 3f was synthesized from t-Boc-Dolaproine (1) and 2-(3-chloro-phenyl)-ethylamine (2f) according to General Procedure A.

Yield 3f: 0.202 g (95.3%) $[\alpha]_D 25=-30.95$ (c=1.15 in CHCl$_3$) M.w.: 424.953 C$_{22}$H$_{33}$N$_2$O$_4$Cl [2S-[2R*[1S*, 2S*]]]-2-[1-methoxy-2-methyl-3-oxo-3-[[2-(2-chloro-phenyl)-ethyl]amino]propyl]-1-pyrrolidinecarboxylic acid, 1,1-dimethylethylester (3g)

Compound 3g was synthesized from t-Boc-Dolaproine (1) and 2-(2-chloro-phenyl)-ethylamine (2g) according to General Procedure A.

Yield 3g: 0.194 g (91.7%) $[\alpha]_D 25=-39.36$ (c=1.71 in CHCl$_3$) M.w.: 424.953 C$_{22}$H$_{33}$N$_2$O$_4$Cl

[2S-[2R*[1S*, 2S*, 3(1S*, 2S*)]]]-2-[1-methoxy-2-methyl-3-oxo-3-[[1-phenyl-1-hydroxy-2-propyl]methylamino]propyl]-1-pyrrolidinecarboxylic acid, 1,1-dimethylethylester (3h)

Compound 3h was synthesized from t-Boc-Dolaproine (1) and (1R, 2R)-(−)-2-methylamino-1-phenylpropan-1-ol (2h) according to General Procedure A.

Yield 3h: 0.14 g (64%) $[\alpha]_D 25 = -184.7$ (c=0.17 in CHCl$_3$) Anal. Calcd for C$_{24}$H$_{38}$N$_2$O$_5$ M.w.: 434.56

[2S-[2R*[1S*, 2S*, 3(1R*, 2S*)]]]-2-[1-methoxy-2-methyl-3-oxo-3-[[1-phenyl-1-hydroxy-2-propyl]amino]propyl]-1-pyrrolidinecarboxylic acid, 1,1-dimethylethylester (3i)

Compound 3i was synthesized from t-Boc-Dolaproine (1) and (1S, 2R)-norephedrine (2i) according to General Procedure A. In this case at the end drying colorless crystals were obtained.

Yield 3i: 0.145 g (69%) M.p.: 55°–57° C. $[\alpha]_D 25 = +8.8$ (c= 0.42 in CHCl$_3$) Anal. Calcd for C$_{23}$H$_{36}$N$_2$O$_5$ M.w.: 420.54

[2S-[2R*[1S*, 2S*, 3(1R*, 2R*)]]]-2-[1-methoxy-2-methyl-3-oxo-3-[[1-phenyl-1-hydroxy-2-propyl]amino]propyl]-1-pyrrolidinecarboxylic acid, 1,1-dimethylethylester (3j)

Compound 3j was synthesized from t-Boc-Dolaproine (1) and D(+)-(1S, 2S)-norephedrine (2j) according to General Procedure A. In this case at the end drying colorless crystals were obtained.

Yield 3j: 0.204 g (97.6%) M.p.: 65°–67° C. $[\alpha]_D 25=+7.0$ (c=0.43 in CHCl$_3$) M.w.: 420.54 C$_{23}$H$_{36}$N$_2$O$_5$

[2S-[2R*[1S*, 2S*, 3(1S*, 2R*)]]]-2-[1-methoxy-2-methyl-3-oxo-3-[[1-phenyl-1-hydroxy-2-propyl]amino]propyl]-1-pyrrolidinecarboxylic acid, 1,1-dimethylethylester (3k)

Compound 3k was synthesized from t-Boc-Dolaproine (1) and (1R, 2S)-norephedrine (2k) according to General Procedure A. In this case at the end drying colorless crystals were obtained.

Yield 3k: 0.201 g (96.0%) M.p.: 53°–55° C. $[\alpha]_D 25 = -38.9$ (c=0.36 in CHCl$_3$) M.w.: 420.54 C$_{23}$H$_{36}$N$_2$O$_5$ Synthesis of Peptides 6a–k (shown above). General Procedure B.

A solution of the amide 3a–k (0.2 mmol) in dichloromethane (2 ml) and trifluoroacetic acid (2 ml) was stirred (ice bath under an argon atmosphere) for two hours. The solvent was removed under reduced pressure and the residue dissolved in toluene. Solvent was again removed in vacuum and this operation was repeated. The residue was dried in a desiccator (under vacuum overnight) to afford the trifluoroacetate salt 4a–k as a viscous oil.

To a solution of the trifluoroacetate salt 4a–k (0.2 mmol) in dichloromethane (2 ml, distilled from CaH$_2$) was added the tripeptide (synthesis previously reported) trifluoroacetate salt (5, 0.109 g, 0.2 mmol) followed by triethylamine (0.088 ml, 0.63 mmol) and diethyl phosphorocyanidate (DEPC, 0.036 ml, 93%, 0.22 mmol, ice bath). The solution was stirred under argon for two hours. The solvent was removed (under vacuum at room temperature) and the residue was chromatographed (silica gel column using acetone-hexane 3:2 as eluent). After the evaporation of solvent from the fractions (selected by TLC behavior) 2 ml of dry dichloromethane was added evaporated. The residue was dried in a desiccator under vacuum overnight to yield a white fluffy solid.

[2S-[1[1R*(R*),2S],2R*[1S*,2S*]]]-N,N-dimethyl-L-valyl-N-[2-methoxy-4-[2-[1-methoxy-2-methyl-3-oxo-3-[[2-(3,4-dimethoxy-phenyl)-ethyl]amino]propyl]-1-pyrrolidinyl-1-(methylpropyl)-4-oxobutyl]-N-methyl-L-valineamide (6a)

Compound 6a was synthesized from trifluoroacetate salt 4a (from amide 3a) and tripeptide trifluoroacetate salt 5 by General Procedure B.

Yield 6a: 128 mg (84%) M.p.: 145°–147° C. $[\alpha]_D 25=-32$ (c=0.2 in CHCl$_3$) Anal. Calc.: C$_{41}$H$_{71}$N$_5$O$_8$ Mw.: 762.018 [2S-[1[1R*(R*),2S*],2R*[1S*,2S*]]]-N,N-dimethyl-L-valyl-N-[2-methoxy-4-[2-[1-methoxy-2-methyl-3-oxo-3-[[2-(4-nitro-phenyl)-ethyl]amino]propyl]-1-pyrrolidinyl-1-(methylpropyl)-4-oxo butyl]-N-methyl-L-valineamide (6b)

Compound 6b was synthesized from trifluoroacetate salt 4e (from amide 3b) and tripeptide trifluoroacetate salt 5 by General Procedure B.

Yield 6b: 129 mg (87%) M.p.: 73°–76° C. $[\alpha]_D 25=-45$ (c=0.08 in CHCl$_3$) Anal. Calc.: C$_{39}$H$_{66}$N$_6$O$_8$ Mw.: 746.965 [2S-[1[1R*(R*),2S*],2R*[1S*,2S*]]]-N,N-dimethyl-L-valyl-N-[2-methoxy-4-[2-[1-methoxy-2-methyl-3-oxo-3-[[2-(4-chlor-phenyl)-ethyl]amino]propyl]-1-pyrrolidinyl-1-(methylpropyl)-4-oxo butyl]-N-methyl-L-valineamide (6c)

Compound 6c was synthesized from trifluoroacetate salt 4c (from amide 3c) and tripeptide trifluoroacetate salt 5 by General Procedure B.

Yield 6c: 125 mg (85%) M.p.: 75°–78° C. $[\alpha]^D{}_{25}:-47.9$ (c=0.19 in CDCl3) Anal. Calc.: C$_{39}$H$_{66}$N$_5$O$_6$Cl Mw.: 736.411 [2S-[1 [1R*(R*),2S*],2R*[1S*, 2S*]]]-N,N-dimethyl-L-valyl-N-[2-methoxy-4-[2-[1-methoxy-2-methyl-3-oxo-3-[[2-(4-chlor-phenyl)-etthyl]amino]propyl]-

1-pyrrolidinyl-1-(methylpropyl)-4-oxo butyl]-N-methyl-L-valineamide (6d)

Compound 6d was synthesized from trifluoroacetate salt 4d (from amide 3d) and tripeptide trifluoroacetate salt 5 by General Procedure B.

Yield 6d: 0.105 g (72.8%) M.p.: 76°–78° C. $[\alpha]_D 25=-44.81$ (c=0.27 in $CHCl_3$) Anal. Calc.: $C_{39}H_{66}N_5O_6F$ Mw.: 719.958 [2S-[1 [1R*(R*),2S*],2R*[1S*,2S*]]]-N,N-dimethyl-L-valyl-N-[2-methoxy-4-[2-[1-methoxy-2-methyl-3-oxo-3-[[2-(4-bromo-phenyl)-ethyl]amino]propyl]-1-pyrrolidinyl-1-(methylpropyl)-4-oxo butyl]-N-methyl-L-valineamide (6e)

Compound 6e was synthesized from trifluoroacetate salt 4e (from amide 3e) and tripeptide trifluoroacetate salt 5 by General Procedure B.

Yield 6e: 0.113 g (72.7%) M.p.: 107°–109° C. $[\alpha]^D{}_{25}$:– 41.76 (c=0.17 in CDCl3) Anal. Calc.: $C_{39}H_{66}N_5O_6Br$ Mw.: 780.867 [2S-[1[1R*(R*),2S*],2R*[1S*,2S*]]]-N,N-dimethyl-L-valyl-N-[2-methoxy-4-[2-[1-methoxy-2-methyl-3-oxo-3-[[2-(3-chlor-phenyl)-ethyl]amino]propyl]-1-pyrrolidinyl-1-(methylpropyl)-4-oxo butyl]-N-methyl-L-valineamide (6f)

Compound 6f was synthesized from trifluoroacetate salt 4f (from amide 3f) and tripeptide trifluoroacetate salt 5 by General Procedure B.

Yield 6f: 0.103 g (69.7%) M.p.: 79°–81° C. $[\alpha]^D{}_{25}$: –41.79 (c=0.28 in CDCl3) Anal. Calc.: $C_{39}H_{66}N_5O_6Cl$ Mw.: 736.411 [2S-[1[1R*(R*),2S*],2R*[1S*,2S*]]]-N,N-dimethyl-L-valyl-N-[2-methoxy-4-[2-[1-methoxy-2-methyl-3-oxo-3-[[2-(2-chlor-phenyl)-ethyl]amino]propyl]-1-pyrrolidinyl-1-(methylpropyl)-4-oxo butyl]-N-methyl-L-valineamide (6g)

Compound 6g was synthesized from trifluoroacetate salt 4g (from amide 3g) and tripeptide trifluoroacetate salt 5 by General Procedure B.

Yield 6g: 0.105 g (71.3%) M.p.: 75°–77° C. $[\alpha]^D{}_{25}$: –44.17 (c=0.36 in CDCl3) Anal. Calc.: $C_{39}H_{66}N_5O_6Cl$ Mw.: 736.411 [2S-[1[1R*(R*),2S*],2R*[1S*,2S*,3(1S*, 2S*)]]]-N,N-dimethyl-L-valyl-N-[2-methoxy-4-[2-[1-methoxy-2-methyl-3-oxo-3-[[1-phenyl-1-hydroxy-2-propyl] methylamino]propyl]- 1-pyrrolidinyl-1-(methylpropyl)-4-oxobutyl]-N-methyl-L-valineamide valineamide (6h)

Compound 6h was synthesized from trifluoroacetate salt 4g (from amide 3h) and tripeptide trifluoroacetate salt 5 by General Procedure B.

Yield 6h: 92 mg (62%) M.p.: 108°–110° C. $[\alpha]_D 25=-70$ (c=0.13 in $CHCl_3$) Anal. Calc.: $C_{41}H_{71}N_5O_7$ Mw.: 746.018 [2S-[1[1R*(R*),2S*],2R*[1S*,2S*, 3(1R*, 2S*)]]]-N,N-dimethyl-L-valyl-N-[2-methoxy-4-[2-[1-methoxy-2-methyl-3-oxo-3-[[1-phenyl-1-hydroxy-2-propyl]amino]propyl]-1-pyrrolidinyl-1-(methylpropyl)-4-oxobutyl]-N-methyl-L-valine amide (6i)

Compound 6i was synthesized from trifluoroacetate salt 4i (from amide 3i) and tripeptide trifluoroacetate salt 5 by General Procedure B.

Yield 6i: 0.101 g (69%) M.p.: 92°–94° C. $[\alpha]^D{}_{25}$: –20 (c=0.12 in CDCl3) Anal. Calc.: $C_{40}H_{69}N_5O_7$ M.w.: 731.992 [2S-[1[1R*(R*),2S*],2R*[1S*,2S*, 3(1R*,2R*)]]]-N,N-dimethyl-L-valyl-N-[2-methoxy-4-[2-[1-methoxy-2-methyl-3-oxo-3-[[1-phenyl-1-hydroxy-2-propyl]amino]propyl]-1-pyrrolidinyl-1-(methylpropyl)-4-oxobutyl]-N-methyl-L-valineamide ( 6j )

Compound 6j was synthesized from trifluoroacetate salt 4j (from amide 3j) and tripeptide trifluoroacetate salt 5 by General Procedure B.

Yield 6j: 0.110 g (75.4%) M.p.: 108°–110° C. $[\alpha]_D 25=-24.05$ (c=0.37 in $CHCl_3$) Anal. Calc.: $C_{40}H_{69}N_5O_7$ Mw.: 731.992 [2S-[1[1R*(R*),2S*],2R*[1S*,2S*, 3(1S*, 2R*)]]]-N,N-dimethyl-L-valyl-N-[2-methoxy-4-[2-[1-methoxy-2-methyl-3-oxo-3-[[1-phenyl-1-hydroxy-2-propyl]amino]propyl]-1-pyrrolidinyl-1-(methylpropyl)-4-oxobutyl]-N-methyl-L-valine amide (6k)

Compound 6k was synthesized from trifluoroacetate salt 4k (from amide 3k) and tripeptide trifluoroacetate salt 5 by General Procedure B.

Yield 6k: 0.098 g (67%) M.p.: 100°–102° C. $[\alpha]^D{}_{25}$: –39.26 (c=0.27 in CDCl3) Anal. Calc.: $C_{40}H_{69}N_5O_7$ Mw.: 731.992

The extraordinary inhibition of cell growth shown by the tetrapeptide 6a–k against six major types of human cancer and against the murine P388 lymphocytic leukemia cell line has been presented in Table 1–2, below.

TABLE 1

| | | Biological activity of Peptides 6a–g | | | | | | |
|---|---|---|---|---|---|---|---|---|
| | Cell type | Cell line | 6a | 6b | 6c | 6d | 6e | 6f | 6g |
| Mouse leukemia cell ED-50 (µg/ml) | | P-388 | 0.003500 | 0.045900 | 0.005530 | 0.00372 | 0.00515 | 0.00225 | 0.000289 |
| Human cancer cell GI-50 (µg/ml) | Ovarian | OVCAR-3 | 0.000007 | 0.00024 | <0.000001 | 0.000016 | 0.00015 | <0.000001 | <0.000001 |
| | CNS | SF-295 | 0.000029 | 0.00035 | 0.000010 | 0.000046 | 0.00043 | 0.000028 | <0.000001 |
| | Renal | A498 | 0.000016 | 0.00064 | 0.00062 | 0.000059 | 0.00046 | <0.000001 | <0.000001 |
| | Lung-NSC | NCI-460 | 0.000031 | 0.00028 | <0.000001 | 0.000025 | 0.00027 | <0.000001 | <0.000001 |
| | Colon | KM20L2 | 0.000025 | 0.00030 | <0.000001 | 0.00033 | 0.00032 | 0.0000007 | <0.000001 |
| | Melanoma | SK-MEL-3 | 0.000018 | 0.00012 | <0.000001 | 0.000044 | 0.00038 | <0.000001 | <0.000001 |
| | Ovarian | OVCAR-3 | 0.000061 | 0.00065 | <0.000001 | 0.000050 | 0.00050 | <0.000001 | <0.000001 |
| | CNS | SF-295 | 0.000083 | >0.01 | 0.0019 | >0.01 | >0.01 | >0.01 | >0.01 |
| Human cancer cell TGI (µg/ml) | Renal | A498 | >0.0001 | >0.01 | >0.01 | 0.0028 | >0.01 | 0.0017 | 0.002 |
| | Lung-NSC | NCI-460 | 0.000094 | 0.0012 | 0.0011 | 0.00014 | 0.0012 | 0.00010 | 0.00011 |
| | Colon | KM20L2 | 0.000061 | 0.0013 | 0.0011 | 0.0029 | 0.0041 | 0.0017 | 0.00038 |
| | Melanoma | SK-MEL-3 | 0.000058 | 0.0013 | >0.01 | >0.01 | >0.01 | >0.01 | >0.01 |
| Human cancer cells LC-50 (µg/ml) | Ovarian | OVCAR-3 | >0.0001 | >0.01 | >0.01 | 0.00096 | 0.0094 | 0.00076 | >0.01 |
| | CNS | SF-295 | >0.0001 | >0.01 | >0.01 | >0.0001 | >0.01 | >0.01 | >0.01 |
| | Renal | A498 | >0.0001 | >0.01 | >0.01 | >0.0001 | >0.01 | >0.01 | >0.01 |
| | Lung-NSC | NCI-460 | >0.0001 | >0.01 | >0.01 | >0.0001 | >0.01 | >0.01 | >0.01 |
| | Colon | KM20L2 | >0.0001 | >0.01 | >0.01 | >0.0001 | >0.01 | >0.01 | >0.01 |
| | Melanoma | SK-MEL-3 | >0.0001 | >0.01 | >0.01 | >0.0001 | >0.01 | >0.01 | >0.01 |

TABLE 2

Biological activity of Peptides 6h–k

| | Cell type | Cell line | 6h | 6i | 6j | 6k |
|---|---|---|---|---|---|---|
| Mouse leukemia cell ED-50 (μg/ml) | | P-388 | 0.001710 | 0.000503 | 0.000321 | 0.000434 |
| Human cancer cell GI-50 (μg/ml) | Ovarian | OVCAR-3 | 0.00006 | 0.000021 | 0.0000097 | 0.00017 |
| | CNS | SF-295 | 0.00031 | 0.000016 | 0.00034 | 0.00060 |
| | Renal | A498 | 0.00099 | 0.0000027 | 0.000096 | 0.00075 |
| | Lung-NSC | NCI-460 | 0.00006 | 0.000025 | 0.000026 | 0.00030 |
| | Colon | KM20L2 | 0.00023 | 0.00011 | 0.000022 | 0.00029 |
| | Melanoma | SK-MEL-3 | 0.00030 | 0.00058 | 0.000044 | 0.00058 |
| Human cancer cell TGI (μg/ml) | Ovarian | OVCAR-3 | 0.0009 | 0.000042 | 0.000046 | 0.00053 |
| | CNS | SF-295 | >0.01 | 0.00024 | >0.01 | >0.01 |
| | Renal | A498 | >0.01 | 0.0000086 | 0.0097 | >0.01 |
| | Lung-NSC | NCI-460 | 0.0014 | >0.01 | 0.00011 | 0.001 |
| | Colon | KM20L2 | 0.0038 | 0.0070 | 0.00052 | 0.0013 |
| | Melanoma | SK-MEL-3 | >0.01 | >0.01 | >0.01 | >0.01 |
| Human cancer cells LC-50 (μg/ml) | Ovarian | OVCAR-3 | >0.01 | 0.000088 | >0.01 | >0.01 |
| | CNS | SF-295 | >0.01 | >0.01 | >0.01 | >0.01 |
| | Renal | A498 | >0.01 | 0.00029 | >0.01 | >0.01 |
| | Lung-NSC | NCI-460 | >0.01 | >0.01 | >0.01 | >0.01 |
| | Colon | KM20L2 | >0.01 | >0.01 | >0.01 | >0.01 |
| | Melanoma | SK-MEL-3 | >0.01 | >0.01 | >0.01 | >0.01 |

From the foregoing, it is readily apparent that a useful embodiment of the present invention has been herein described and illustrated which fulfills all of the aforestated objectives in a remarkably unexpected fashion. It is of course understood that such modification, alterations and adaptations as may readily occur to the artisan confronted with this disclosure are intended within the spirit of this disclosure which is limited only by the scope of the claims appended hereto.

Accordingly, what we claim is:

1. A compound having the following structural formula

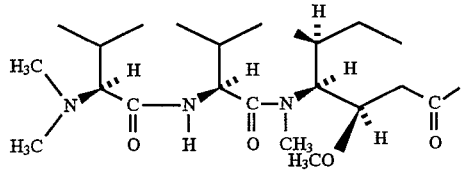

-continued

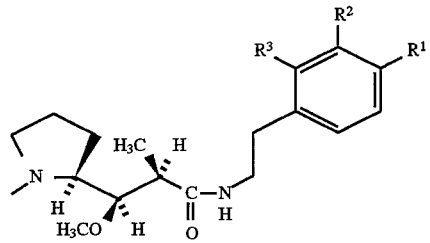

wherein $R^1$ is selected from the group consisting of $OCH_3$, $NO_2$, F, Cl, Br, and H; $R^2$ is selected from the group consisting of $OCH_3$, H, and Cl; and $R^3$ is selected from the group consisting of H and Cl, provided that if $R^1$ is $NO_2$, Cl, F, or Br, $R^2=R^3=H$; that if $R^2=Cl$ then $R^1=R^3=H$; that if $R^3=Cl$ then $R^2=R^3=H$ and that if $R^1=OCH_3$, then $R^2=R^1$ and $R^3=H$.

2. A compound having the following structural formula

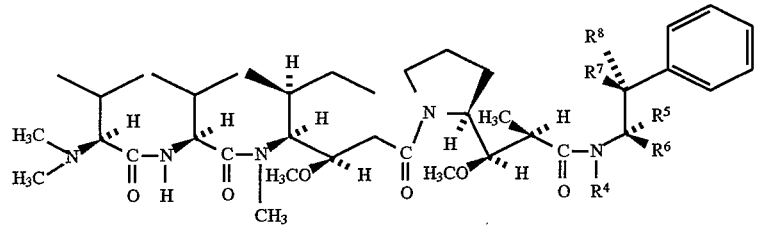

wherein $R^4$ is selected from the group consisting of H and $CH_3$, $R^5$ is selected from the group consisting of H and $CH_3$, $R^6$ is selected from the group consisting of $CH_3$ and H, $R^7$ is selected from the group consisting of H and OH, and $R^8$ is selected from the group consisting of H and OH; provided that either $R^7$ or $R^8$=OH, that at least one of $R^4$, $R^5$ and $R^6$=$CH_3$ and that at least two of $R^4$, $R^5$, $R^6$, $R^9$ and $R^8$=H.

3. A method of inhibiting the growth of cancer cells selected from the group of cell lines consisting of P388, OVCAR-3, SF295, A498, NCI-460, KM20L2 and SK-MEL-3, comprising of engaging said selected cell with a cell growth inhibitory amount of the compound having the following structural formula:

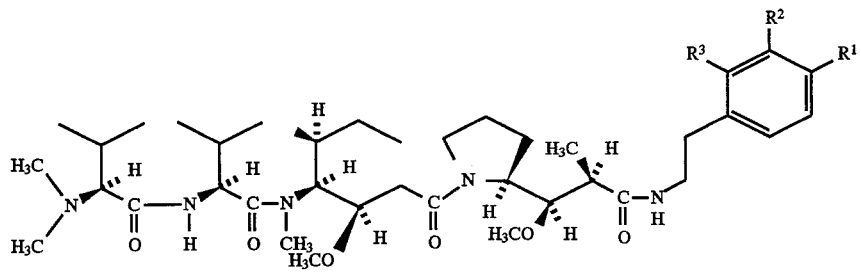

wherein $R^1$ is selected from the group consisting of $OCH_3$, $NO_2$, F, Cl, Br, and H; $R^2$ is selected from the group consisting of $OCH_3$, H, and Cl; and $R^3$ is selected from the group consisting of H and Cl, provided that if $R^1$ is $NO_2$, Cl, F, or Br, $R^2$=$R^3$=H; that if $R^2$=Cl then $R^1$=$R^3$=H; that if $R^3$=Cl then R=$R^2$=H and that if $R^1$=$OCH_3$ then $R^2$=$R^1$ and $R^3$=H.

4. A method of inhibiting the growth of cancer cells selected from the group of cell lines consisting of P388, OVCAR-3, SF295, A498, NCI-460, KM20L2 and SK-MEL-3, comprising of engaging said cell line with a cell growth inhibitory amount of the compound having the following structural formula:

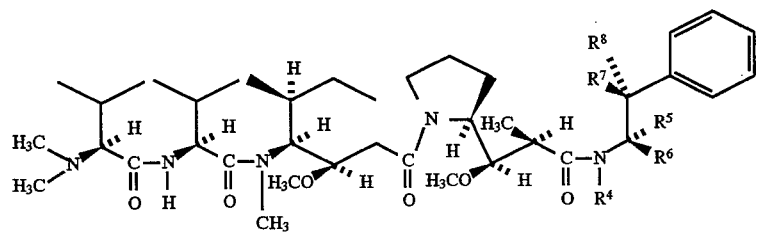

wherein $R^4$ is selected from the group consisting of H and $CH_3$, $R^5$ is selected from the group consisting of H and $CH_3$, $R^6$ is selected from the group consisting of $CH_3$ and H, $R^7$ is selected from the group consisting of H and OH, and $R^8$ is selected from the group consisting of H and OH; provided that either $R^7$ of $R^8$=OH, that at least one of $R^4$, $R^5$ and $R^6$=$CH_3$ and that at least two of $R^4$, $R^5$, $R^6$, $R^7$ and $R^8$=H.

5. A compound according to claim 1 wherein $R^1$=H or Cl, $R^2$=H or Cl and $R^3$=Cl or H.

6. A method according to claim 3 wherein $R^1$=H or Cl, $R^2$=H or Cl, and $R^3$=Cl or H.

7. A compound according to claim 2 wherein $R^4$=H, $R^5$=$CH_3$, $R^6$=H, $R^7$=OH or H, $R^8$=OH or H and $R^7 \neq R^8$.

8. A method according to claim 4 wherein $R^4$=H, $R^5$=$CH_3$, $R^6$=H, $R^7$=OH or H, $R^8$=OH or H, and $R^7 \neq R^8$.

* * * * *